United States Patent
Astarita et al.

(10) Patent No.: US 12,019,047 B2
(45) Date of Patent: Jun. 25, 2024

(54) METHOD OF USING CHEMICAL TAGS TO IMPROVE THE IDENTIFICATION, QUANTIFICATION AND SPATIAL LOCALIZATION OF COMPONENTS IN A SAMPLE

(71) Applicant: Waters Technologies Corporation, Milford, MA (US)

(72) Inventors: Giuseppe Astarita, Hopkinton, MA (US); Darryl W. Brousmiche, Grafton, MA (US)

(73) Assignee: Waters Technologies Corporation, Millord, MA (US)

( * ) Notice: Subject to any disclaimer, the term of this patent is extended or adjusted under 35 U.S.C. 154(b) by 106 days.

(21) Appl. No.: 17/823,360

(22) Filed: Aug. 30, 2022

(65) Prior Publication Data
US 2023/0013977 A1 Jan. 19, 2023

Related U.S. Application Data (62) Division of application No. 16/077,859, filed as application No. PCT/US2017/018327 on Feb. 17, 2017, now Pat. No. 11,460,438.

(60) Provisional application No. 62/359,390, filed on Jul. 7, 2016, provisional application No. 62/297,070, filed on Feb. 18, 2016.

(51) Int. Cl.
*G01N 27/623* (2021.01)
*G01N 27/447* (2006.01)
(Continued)

(52) U.S. Cl.
CPC ..... *G01N 27/623* (2021.01); *G01N 27/44726* (2013.01); *G01N 27/622* (2013.01);
(Continued)

(58) Field of Classification Search
None
See application file for complete search history.

(56) References Cited

U.S. PATENT DOCUMENTS

| 5,516,931 A | 5/1996 | Giese et al. |
| 2002/0175278 A1 | 11/2002 | Whitehouse |

(Continued)

FOREIGN PATENT DOCUMENTS

| EP | 3384518 A1 | 10/2018 |
| WO | 2007140380 A2 | 12/2007 |
| WO | 2012097451 A1 | 7/2012 |
| WO | 2014021960 A1 | 2/2014 |
| WO | 2014210225 A1 | 12/2014 |

OTHER PUBLICATIONS

International Search Report and the Written Opinion from Corresponding PCT/US2017/018327; Completed on Apr. 2, 2017; dated Apr. 25, 2017.

(Continued)

*Primary Examiner* — Xiaoyun R Xu
(74) *Attorney, Agent, or Firm* — WOMBLE BOND DICKINSON (US) LLP; Deborah M. Vernon; Ricardo Joseph (57) ABSTRACT

The present disclosure relates to a method for using chemical tags which have two or more sites for ionization to improve quantification and identification of components of interest from a complex mixture. This method relies on first selectively reacting one or more component in a sample with a chemical tag having two or more sites for ionization, followed by separation of components based on charge status, and finally characterization of each component to identify the same. Additionally disclosed are compounds useful as chemical tags in the disclosed methods.

3 Claims, 2 Drawing Sheets

(51) Int. Cl.
    *G01N 27/622*     (2021.01)
    *G01N 30/06*     (2006.01)
    *G01N 30/72*     (2006.01)
    *G01N 33/58*     (2006.01)
    *G01N 33/68*     (2006.01)

(52) U.S. Cl.
    CPC ......... *G01N 30/06* (2013.01); *G01N 30/7266* (2013.01); *G01N 33/58* (2013.01); *G01N 33/6851* (2013.01); *G01N 2030/067* (2013.01)

(56) References Cited

U.S. PATENT DOCUMENTS

| | | |
|---|---|---|
| 2012/0107942 A1 | 5/2012 | Baginski |
| 2015/0219598 A1 | 8/2015 | Mordehai et al. |
| 2017/0254777 A1 | 9/2017 | Olivos et al. |
| 2018/0033598 A1 | 2/2018 | Ubhi et al. |

OTHER PUBLICATIONS

Leriche et al. "Investigation of Dendriplexes by Ion Mobility-Mass Spectrometry." Molecules. 19(2014): 20731-20750.

Paglia G, Kliman M, Claude E, Geromanos S, Astarita G. Applications of ion-mobility mass spectrometry for lipid nalysis. Anal Bioanal Chem. Jul. 2015;407(17):4995-5007. doi: 10.1007/s00216-015-8664-8. Epub Apr. 17, 2015.

Pubchem Summary for CID 102271434, Deposit Date Dec. 25, 2015 (Dec. 25, 2015), pp. 1-9.

METHOD OF USING CHEMICAL TAGS TO IMPROVE THE IDENTIFICATION, QUANTIFICATION AND SPATIAL LOCALIZATION OF COMPONENTS IN A SAMPLE

CROSS-REFERENCE TO RELATED APPLICATIONS

This application is a divisional application of U.S. patent application Ser. No. 16/077,859 filed Aug. 14, 2018 which is a National Stage Application of International Application No. PCT/US2017/018327, filed Feb. 17, 2017, which claims the benefit of U.S. Provisional Patent Application No. 62/297,070, filed Feb. 18, 2016, and U.S. Provisional Patent Application No. 62/359,390, filed-by reference. Each of the foregoing applications is incorporated herein by reference in its entirety.

FIELD

This invention relates generally to a method of using an ionization state of certain molecules in a complex mixture to isolate, and potentially quantify, individual components therein. In particular, the present disclosure relates to use of chemical tags that contain two or more potential sites for ionization which selectively react with certain components of a complex mixture. Components of the sample are then separated by charge state, with the multiply-charged, tagged components being easily separated from the other components, followed by characterization of all components therein.

BACKGROUND

Biological samples may contain many different types of compounds, including naturally occurring components such as lipids and proteins, as well as unnaturally occurring components such as small molecule compounds (e.g., medications), which may be present in the sample. Analysis of biological samples can lead to diagnosis of disease, determination of exposure to, and efficacy of, medications, and the presence or absence of components of particular interest, among many other uses.

One means of identifying components in a sample is by using chemical modifiers, also known as probes or labels, which have shown utility in the biology and biotechnology realms as a means to label specific molecules such as proteins, antibodies or amino acids. There are currently several labeling methods for tracking biomolecules such as electrochemical, optical (including fluorophores), mass change and calorimetric chemical tags. However, while these chemical modifiers may help in the visualization of a particular component in a solution, they cannot be used to separate components out of a complex sample and characterize them.

Another means to determine the components of a biological sample is to subject it to more traditional analytical methods, such as mass spectrometry analysis of the complex mixture of materials in a biological sample. An example of this is shotgun lipidomics. However, such methods often fail to deliver accurate results because of the chemical complexity of the components of samples, i.e., multiple lipid species. Thus, this type of approach is often associated with the inability to distinguish isobaric species present in a complex sample. Thus, this method also cannot adequately distinguish and quantify all relevant species from biological samples.

Currently, there is a need for improved techniques for rapid separation and identification of components from complex mixtures, such as biological samples.

SUMMARY OF THE INVENTION

The present disclosure relates to a method for using chemical tags which have two or more sites for ionization to improve quantification, identification and/or spatial localization of components of interest from a complex mixture. This method relies on selectively reacting one or more component in a sample with a chemical tag having two or more sites for ionization, followed by separation of components based on charge status, and finally characterization of each component to ascertain its identity.

In particular, the present disclosure relates to a method of using the ionization state of certain molecules in a complex sample to isolate, and potentially quantify, individual components therein. Methods disclosed herein are useful for the identification, quantification and/or spatial localization of the components of a sample containing one or more components which may be reacted with a chemical tag containing two or more sites of possible ionization.

In one embodiment, the present disclosure relates to a method of identifying components of a sample comprising 1) selectively reacting one or more components in the sample with a chemical tag which has two or more sites for ionization; 2) separating the components using ion mobility spectrometry or capillary electrophoresis; and 3) analyzing the sample to identify the components therein.

In one embodiment, the present disclosure relates to use of a chemical tag according to one of Formulae (I), (II) or (III):

or a salt thereof, wherein:
each Y is independently $-(CH_2CH_2)_nW-$, $-(CH_2)_nW-$, $(CH_2CH_2W)_n$, $-(CH_2W)_n(CH_2)_k-$, $-(CH_2CH_2W)_n(CH_2)_k-$, $-(CH_2)_p-W-C(O)-W-(CH_2)_p-$, each Y' is independently —(CH$_2$CH$_2$)$_n$W—, —(CH$_2$)$_n$W—, (CH$_2$CH$_2$W)$_n$, —(CH$_2$W)$_n$(CH$_2$)$_k$—, —(CH$_2$CH$_2$W)$_n$(CH$_2$)$_k$—, —(CH$_2$)$_p$—W—C(O)—W—(CH$_2$)$_p$—, each Y" is independently —(CH$_2$CH$_2$)$_n$W—, —(CH$_2$)$_n$W—, (CH$_2$CH$_2$W)$_n$, —(CH$_2$W)$_n$(CH$_2$)$_k$—, —(CH$_2$CH$_2$W)$_n$(CH$_2$)$_k$—, or —(CH$_2$)$_p$—W—C(O)—W—(CH$_2$)$_p$—;

each Y$_1$ is independently: —(CH$_2$)$_n$W(CH$_2$)$_n$—, —OC(O)—(CH$_2$)$_{1-4}$—, —OC(O)—(CH$_2$)$_{1-4}$W— or absent;

each X is independently: —N$^+$(C$_1$-C$_6$alkyl)$_3$, —S(O)$_2$(OH), —OS(O)$_2$(OH), —NH—C(=NH)NH$_2$, —OP(O)(OH)$_2$, —P(O)(OH)$_2$, —C(O)N(C$_1$-C$_6$alkyl)$_2$, —N(C$_1$-C$_6$alkyl)$_2$, —NHC(O)(OC$_1$-C$_6$alkyl), —CO$_2$H, —C(O)NH$_2$, —C(O)NH(C$_1$-C$_6$alkyl), or —C(O)(OC$_1$-C$_6$alkyl);

each RG is independently isocyanate, thioisocyanate, succinimidyl ester, succinimidyl carbamate, carboxylic acid, amine, or aldehyde;

each W is independently N(C$_1$-C$_6$ alkyl) NH, O, S, or absent;

each Z is independently CH or N;

each R is independently halo, —OH, —CN, C$_1$-C$_3$ alkyl, C$_3$-C$_6$ cycloalkyl, C$_1$-C$_3$ alkoxy, C$_1$-C$_3$ haloalkyl or C$_1$-C$_3$ haloalkoxy;

each n is independently 0-4;
each p is independently 0-6;
each k is independently 0-6; and
m is 0-3;

and wherein each (CH$_2$) or (CH$_2$CH$_2$) segment of Y, Y' and Y" may be optionally and independently substituted with 1 or 2 groups selected from methyl, ethyl, —OH, halo or carbonyl and wherein each Y, Y' and Y" is attached to an X group; provided that n and k are not both 0 when Y, Y' or Y" is —(CH$_2$W)$_n$(CH$_2$)$_k$— or —(CH$_2$CH$_2$W)$_n$(CH$_2$)$_k$—.

In a further embodiment, the present disclosure relates to use of a chemical tag which is according to one of formulae (Ia), (Ib), (IIa), (IIb), (IIIa), or (IIIb):

(Ia)

(Ib)

(IIa)

(IIb)

(IIIa)

(IIIb)

or a salt thereof, wherein the variables are as described for formula (I), (II) and (III), above.

In another embodiment, the present disclosure relates to use of a chemical tag which is according to one of Formulae (IV), (V), (VI), (VII), (VIII) or (IX):

or a salt thereof; wherein each Q is N(C$_1$-C$_3$alkyl), NH or O;

each T is H, methyl or —OH;

each Y$_1$ is —(CH$_2$)$_{1-3}$NH—, —OC(O)(CH$_2$)$_{1-3}$—, —NHC(O)(CH$_2$)$_{1-3}$—, —C(O)O(CH$_2$)$_{1-3}$—, —C(O)NH(CH$_2$)$_{1-3}$—, —(CH$_2$)$_{1-3}$—, or absent;

each X is independently —N$^+$(C$_1$-C$_6$alkyl)$_3$, —S(O)$_2$(OH), —OS(O)$_2$(OH), —NHC(=NH)NH$_2$, —OP(O)(OH)$_2$, P(O)(OH)$_2$, —N(C$_1$-C$_6$alkyl)$_2$, or —CO$_2$H; and each RG is isocyanate, thioisocyanate, succinimidyl ester or a succinimidyl carbamate.

Additionally, in accordance with another aspect, the disclosure relates to novel compounds which can be used as chemical tags in the disclosed methods. In one embodiment is a compound selected from the group consisting of:

or a salt thereof; wherein each $R^3$ is independently $C_1$-$C_6$ alkyl; and each $R^4$ is independently —H or $C_1$-$C_6$ alkyl.

The methods of the present disclosure provide several advantages over the prior art. The present methodology may be used for determination of the components of a sample with improved selectivity, sensitivity, specificity and/or mass accuracy over present techniques.

Separation of multiply charged species increases resolution of the components and can allow for more efficient separation of target components from species of same molecular weight (isobaric) as well as from impurities. Additional advantages may include the ability to identify and characterize components such as small molecules, peptides and/or other biologically relevant molecules from a sample, as well as the spatial localization of the same. The present method allows for limited sample preparation and fractionation of the different molecular content of the sample prior to analysis to identify the components therein. In this way, a multi-omics analysis can be conducted in a single acquisition. Additionally, the present methods may lead to shorter time to analyze complex samples, by allowing direct infusion of samples to be analyzed with minimal to no purification. Shorter time to analysis is the result of the need for only limited sample preparation, which allows for direct infusion into the MS.

Furthermore, compounds of the present disclosure can be used for analysis and separation based on charge state for any analyte which is able to react with the chemical tags described herein. Use of chemical tags of the present invention to selectively tag specific compounds in a complex sample potentially increases the separation of isobaric species, improves the signal to noise ratio, and thereby reduces false positive assignments, which in turn increases the accuracy of the results.

DETAILED DESCRIPTION

This invention relates generally to a method of using chemical tags to modify certain components of a complex sample to isolate, potentially quantify, and/or spatially locate, individual components therein based on charge state, followed by characterization of the individual components. In particular, the method disclosed herein allows for selective reaction of certain components of a complex biological sample with a chemical tag containing two or more sites for ionization; separation of the components based on charge state using ion mobility (IM) or capillary electrophoresis (CE); and analysis of the sample to identify the components therein. The methods of the present disclosure can allow rapid analysis of biological samples without requiring much, if any, sample preparation.

The methods of the present disclosure provide several advantages over the prior art. The present methodology may be used for the determination of the components of a sample with improved selectivity, sensitivity, specificity and/or mass accuracy over present techniques.

Definitions

As used herein, the term "isobaric species" refers to a chemical compound or molecule that have the same molecular weight. Isobaric species can be made up of different atoms, or the same atoms connected in a different way.

"Dendrimer-type molecule" means a repetitively branched molecule with a single chemically addressable group (i.e., focal point) which may be useful to attaching to a molecule in need of chemical tagging. "Dendrimer-type molecules" as useful in the present invention possess two or more chemical sites which can be ionized and include molecules typically characterized as "dendrimers" and "dendrons", but do not include high molecular weight species such as dendrimer-polymers, hyper-branched polymers and/or polymer brushes. Typically, the terms "dendrimers" and "dendrons" include generation 1, generation 2, or generation 3 molecules, and/or contain no more than 27 ionizable groups. Generation number refers to the "number of repeated branching cycles that are performed during synthesis"

The term "alkyl" means saturated or unsaturated aliphatic straight-chain, branched or cyclic monovalent hydrocarbon radical. Unless otherwise specified, an alkyl group typically has 1 to 6 carbon atoms, i.e., $C_1$-$C_6$-alkyl. As used herein, a "$C_1$-$C_6$-alkyl" group means a radical having from 1 to 6 carbon atoms in a linear, branched or cyclic arrangement, and includes methyl, ethyl, propyl, isopropyl, butyl, isobutyl, sec-butyl, tert-butyl, isopentyl, hexyl, cyclopropyl, cyclo butyl, cyclopentyl, cyclohexyl, ethynyl, ethenyl, propynyl, propenyl, and the like.

The term "reactive group" ("RG") also referred to herein as a "functional group". Both terms are used interchangeably throughout the specification. A RG or functional group allows for the reaction between a component of a sample and a chemical tag according to one of Formulae (I) through (VII). In one embodiment, the RG is a labile group which allows it to react with a nucleophile or nucleophilic group. Alternatively, the RG is a group which enhances the nucleophilicity of a group on the chemical tag, such as an amine, which allows it to react with an electrophilic group of a component in the sample. In some embodiments, the RG group is able to rapidly react with the target molecule or target molecules in the sample. Non-limiting examples of RG groups include, isocyanates, isothiocyanates, succinimidyl esters, succinimidyl carbamates, carboxylic acids, amines, aldehydes, esters, dienes, alkenes and alkynes. Preferred RG groups include, but are not limited to, isocyanates, isothiocyanates, succinimidyl esters, succinimidyl carbamates, carboxylic acids, amines, and aldehydes. As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

The term "ion-mobility-separation" ("IM") is a gas-phase electrophoretic technique that enables the separation of gas-phase lipid ions within a chamber pressurized with a buffer gas, such as purified argon or nitrogen gas. An inert gas is not necessarily elemental and is often a compound gas that have the tendency for non-reactivity is due to the valence, the outermost electron shell, being complete in all the inert gases. This is a tendency, not a rule, as noble gases and other "inert" gases can react to form compounds.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "chromatography" refers to a process in which a chemical mixture carried by a liquid or gas is separated into components as a result of differential distribution of the chemical entities as they flow around or over a stationary liquid or solid phase.

"Spectroscopy" refers to the study of the interaction between matter and electromagnetic radiation. Spectroscopic data is often represented by an emission spectrum, a plot of the response of interest as a function of wavelength or frequency. Exemplary spectroscopic techniques include Mossbauer spectroscopy. X-ray absorption spectroscopy, UV/Vis spectroscopy, atomic absorption spectroscopy, infrared spectroscopy, Raman spectroscopy, microwave spectroscopy, electron spin resonance spectroscopy, nuclear magnetic resonance spectroscopy (NMR), nuclear quadrupole resonance spectroscopy (NQR), nuclear atomic emission spectroscopy, X-ray fluorescence, fluorescence spectroscopy, phosphorescence spectroscopy, atomic fluorescence spectroscopy, and chemiluminescence spectroscopy, each of which can provide unique information about the properties of a chemical species. For example, Raman spectroscopy is a spectroscopic technique used to identify molecules by their characteristic vibrational, rotational and other low-frequency modes.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include (but are not limited to) reverse phase liquid chromatography (RPLC), high performance liquid chromatography (HPLC), ultra-high performance liquid chromatography (UPLC or UHPLC), turbulent flow liquid chromatography (TFLC) (sometimes known as high turbulence liquid chromatography (HTLC) or high throughput liquid chromatography), and carbon dioxide based chromatograpy.

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UHPLC" (sometimes known as "ultra high pressure liquid chromatography") refers to HPLC that occurs at much higher pressures than traditional HPLC techniques.

The term "LC/MS" refers to a liquid chromatograph (LC) interfaced to a mass spectrometer. The term "LC/MS/MS" refers to a liquid chromatograph (LC) interfaced to an instrument that includes two mass spectrometers.

The term "IM-MS" refers to method that separates gas phase ions on a millisecond timescale using ion-mobility spectrometry and uses mass spectrometry on a microsecond timescale to identify components in a sample.

The term "drift time" refers to the time required for lipid ions to cross the ion-mobility separation cell. This net ion motion is usually much slower than the normally occurring random motion. In a semiconductor the charge carriers will typically have different drift velocities for the same electric field. SI unit of mobility is $(m/s)/(V/m)=m^2/(V \cdot s)$. However, mobility is much more commonly expressed in $cm^2/(V \cdot s)=10^{-4} m^2/(V \cdot s)$.

The term "collision cross section" ("CSS") refers to an area that quantifies the likelihood of a scattering event when an incident species strikes a target species. In a hard object approximation, the cross section is the area of the conventional geometric cross section. The collisional cross sections typically denoted a and measured in units of area.

Methods of the Invention

The methods of the present disclosure provide several advantages over the prior art. The present methodology may be used for the determination of the components of a sample with improved selectivity, sensitivity, specificity and/or mass accuracy over present techniques. Separation of multiply charged species increases resolution of components in a mixture, and can allow for more efficient separation of target components from species of similar weight, as well as from impurities. Additional advantages include the ability to identify and characterize components such as small molecules, peptides and/or other biologically relevant molecules from a sample, and the spatial localization of the same. The present method may allow for limited sample preparation and fractionation of the different molecular content of the sample prior to analysis to identify the components there. In this way, a multi-omics analysis may be conducted in a single acquisition. Additionally, the present methods may lead to shorter time to analyze complex samples, by allowing direct infusion of samples to be analyzed with minimal to no purification. In one embodiment, the present disclosure relates to a method of identifying components of a sample comprising 1) selectively reacting one or more components in the sample with a chemical tag which has two or more sites for ionization; 2) separating the components using ion mobility spectrometry or capillary electrophoresis; and 3) analyzing the sample to identify the components therein.

In another embodiment, the present method includes the additional step of separating the molecules in a biological sample using chromatography after the reaction of specific components with a chemical tag. This chromatographic step may then be followed by separation of the ionized molecules of the sample according to the ionization state of the components and analysis of the sample to identify the components therein. In a further embodiment, the present method includes the steps of: 1) selectively reacting a component in the sample with a chemical tag which has two or more sites for ionization; 2) separation of the tagged biological sample by chromatography; 3) ionizing the components of the sample; 4) separating the ionized components of the sample using ion mobility spectrometry or capillary electrophoresis; and 5) analyzing the sample to identify the components therein.

In either of the above two embodiments, the separation of the biological sample by chromatography includes separation by gas chromatography or liquid chromatography. In one aspect of this embodiment, the gas chromatography may be carbon-dioxide based supercritical fluid chromatography. In one aspect of this embodiment, the separation of the biological sample is done using liquid chromatography, wherein the liquid chromatography is selected from ultra-high performance liquid chromatography (UHPLC), traditional low-pressure liquid chromatography, high performance liquid chromatography (HPLC), and hydrophilic interaction chromatography (HILIC). In one aspect of this embodiment, HPLC may refer to normal phase chromatography or reverse phase chromatography (RPC). The resulting method may provide an additional degree of separation and will result increased specificity of components to selectively react with the desired chemical tag, and thus, ultimately enhance identification and relative quantification.

In another embodiment, the present method includes use of any type of mass spectrometer to analyze the sample and identify the components therein (after the separation by ion mobility or capillary electrophoresis) to identify and possibly quantify the individual components of the sample. In one aspect of this embodiment, the present method includes analysis of the separated ionized molecules after ion mobility separation using sector, time-of-flight, quadrupole, ion trap, or Fourier transform ion cyclotron resonance, or by tandem mass spectrometry (MS/MS) (where two or more of the above types are combined in tandem or orthogonally). In one embodiment, the present disclosure includes analysis of the separated ionized molecules after ion mobility separation is done using tandem mass spectrometry (MS/MS).

In yet another embodiment, the present disclosure includes analyzing a sample, comprising selectively reacting one or more component in the sample with a chemical tag which has two or more sites for ionization and an additional functionality, such as a fluorescent moiety or a moiety which is visible in the IR or UV-Vis spectrum, separating components using ion mobility spectrometry or capillary electrophoresis, and analyzing the sample at a plurality of different locations and identifying the components contained in location sampled. In this embodiment, the spatial localization will be enhanced by the additional properties of the chemical tag, which would allow for visualization of tagged components without the need for MS or additional analytical methods.

In one embodiment, the method of the present disclosure may be performed by incorporation ion mobility separation into the Waters Technologies Corporation $MS^E$ process (for example, processes capable with using Xevo® GS-XS QTof, SYNAPT® G2-Si MS, Vion® IMS QTof, all commercially available from Waters Technologies Corporation, Milford, MA). Use of this process for the present method allows an acquisition mode, high definition MS (HDMSE), where co-eluting lipid precursor ions can be separated by ion-mobility before fragmentation, resulting in cleaner MS/MS product-ion spectra. In aspect of this embodiment, the method includes the calculation of the CCS value for the ionized molecules. In a further aspect of this embodiment, the CCS value calculated in the present method is used to assist in the identification of components of the sample. The methods, processes, and techniques in accordance to the present disclosure provide a technological advancement with respect to the information obtained in comparison to the prior art.

In another embodiment, the present disclosure relates to separation of isobaric components from a biological sample based on the charge state of the ionized molecules by first separating the ionized components according to the IM or CE of the ionized components, and then analyzing the ionized components using an analytical technique such as mass spectrometry. In one aspect of this embodiment, the biological sample includes one or more isobaric components, one of which is selectively reacted with a chemical tag of the invention, which can be separated using differential charge status—meaning one isobaric species can be reacted with a chemical tag having two or more possible sites for ionization, while the other isobaric species has a different number of possible sites for ionization, such as one, and the ion separation step is able to separate out the isobaric species based on charge status.

Advantages of the present method include the ability to obtain real-time, high-throughput analysis of biological samples such as dried blood spots, biofluids and tissue-biopsies without performing much, if any, sample preparation. The presently disclosed methodology can be used for determination of individual components from a sample with improved selectivity, sensitivity, specificity, and/or mass accuracy over current separation techniques, while maintaining the ability to rapidly analyze samples.

Compounds of the Invention

Compounds of the present disclosure can be used for analysis and separation based on charge state for any analyte that is able to react with the chemical tags described herein.

In one embodiment, the present disclosure relates to use of a chemical tag according to one of Formulae (I), (II) or (III):

or a salt thereof, wherein:
each Y is independently —(CH$_2$CH$_2$)$_n$W—, —(CH$_2$)$_n$W—, (CH$_2$CH$_2$W)$_n$, —(CH$_2$W)$_n$(CH$_2$)$_k$—, —(CH$_2$CH$_2$W)$_n$(CH$_2$)$_k$—, —(CH$_2$)$_p$—W—C(O)—W—(CH$_2$)$_p$—, $$Y''-Z\diagup_{Y'}^{Y'}Y'\quad\text{or}\quad Y''-\diagup_{Y'}^{Y'}Y';$$

each Y' is independently —(CH$_2$CH$_2$)$_n$W—, —(CH$_2$)$_n$W—, (CH$_2$CH$_2$W)$_n$, —(CH$_2$W)$_n$(CH$_2$)$_k$—, —(CH$_2$CH$_2$W)$_n$(CH$_2$)$_k$—, —(CH$_2$)$_p$—W—C(O)—W—(CH$_2$)$_p$—, $$Y''-Z\diagup_{Y''}^{Y''}Y''\quad\text{or}\quad Y''-\diagup_{Y''}^{Y''}Y'';$$

each Y'' is independently —(CH$_2$CH$_2$)$_n$W—, —(CH$_2$)$_n$W—, (CH$_2$CH$_2$W)$_n$, —(CH$_2$W)$_n$(CH$_2$)$_k$—, —(CH$_2$CH$_2$W)$_n$(CH$_2$)$_k$—, or —(CH$_2$)$_p$—W—C(O)—W—(CH$_2$)$_p$—;
each Y$_1$ is independently: —(CH$_2$)$_n$W(CH$_2$)$_n$—, —OC(O)—(CH$_2$)$_{1-4}$—, —OC(O)—(CH$_2$)$_{1-4}$W— or absent;
each X is independently: —N$^+$(C$_1$-C$_6$alkyl)$_3$, —S(O)$_2$(OH), —OS(O)$_2$(OH), —NH—C(=NH)NH$_2$, —OP(O)(OH)$_2$, —P(O)(OH)$_2$, —C(O)N(C$_1$-C$_6$alkyl)$_2$, —N(C$_1$-C$_6$alkyl)$_2$, —NHC(O)(OC$_1$-C$_6$alkyl), —CO$_2$H, —C(O)NH$_2$, —C(O)NH(C$_1$-C$_6$alkyl), or —C(O)(OC$_1$-C$_6$alkyl);
each RG is independently isocyanate, thioisocyanate, succinimidyl ester, succinimidyl carbamate, carboxylic acid, amine, or aldehyde;
each W is independently N(C$_1$-C$_6$ alkyl) NH, O, S, or absent;
each Z is independently CH or N;
each R is independently halo, —OH, —CN, C$_1$-C$_3$ alkyl, C$_3$-C$_6$ cycloalkyl, C$_1$-C$_3$ alkoxy, C$_1$-C$_3$ haloalkyl or C$_1$-C$_3$ haloalkoxy;
each n is independently 0-4;
each p is independently 0-6;
each k is independently 0-6; and
m is 0-3;

and wherein each (CH$_2$) or (CH$_2$CH$_2$) segment of Y, Y' and Y'' may be optionally and independently substituted with 1 or 2 groups selected from methyl, ethyl, —OH, halo or carbonyl and wherein each Y, Y' and Y'' is attached to an X group; provided that n and k are not both 0 when Y, Y' or Y'' is —(CH$_2$W)$_n$(CH$_2$)$_k$— or —(CH$_2$CH$_2$W)$_n$(CH$_2$)$_k$—.

Chemical Tags

Chemical tags are used in present invention to selectively tag specific compounds in a complex sample potentially increases separation from isobaric species, improving the signal to noise ratio, and thereby reduces false positive assignments, which increases the measurement accuracy of the results.

In one embodiment, the present disclosure relates to use of a chemical tag which has two or more sites of possible ionization. In one aspect of this embodiment, the chemical tag may also contain a fluorescent or ultra-violet (UV) active moiety. In another aspect of this embodiment, the chemical tag may contain a moiety which absorbs in the visible (VIS) spectrum or the infrared (IR) spectrum.

In another embodiment, the present disclosure relates to use of a chemical tag which has two or more site of possible ionization. In one aspect of this embodiment, the groups which have the potential for ionization include, but are not limited to, amine, trialkyl ammonium, guanidine, carboxylic acid, ester (ideally after hydrolysis), amide (ideally after hydrolysis), sulfate, sulfonate, phosphate and/or phosphonate. In one aspect of this embodiment, the ionizable group is a carboxylic acid. In another aspect of this embodiment, the ionizable group is an amine. In another aspect of this embodiment, the ionizable group is a phosphonate. In another aspect of this embodiment, the ionizable group is a phosphate. In another aspect of this embodiment, the ionizable group is a sulfonate. In another aspect of this embodiment, the ionizable group is a guanidinyl. In another aspect of this embodiment, the ionizable group is a trialkyl ammonium group. In another aspect of this embodiment, the ionizable group is a sulfate. In a further aspect of this embodiment, the ionizable group is an ester, which may be hydrolyzed to its corresponding carboxylic acid. In a further aspect of this embodiment, the ionizable group is an amide, which may be hydrolyzed to its corresponding carboxylic acid.

In yet another embodiment, the present disclosure relates to use of a chemical tag which is according to one of formulae (Ia), (Ib), (IIa), (IIb), (IIIa), or (IIIb):

or a salt thereof, wherein the variables are as described for formula (I), (II) and (III), above.

In one aspect of the above embodiments, for any one of Formulae (I), (Ia), (Ib), (II), (IIa), (IIb), (III), (IIIa) or (IIIb), each Y, Y' and Y" is independently selected from —[(CH$_2$)$_{1-2}$OC(O)(CH$_2$)$_{1-2}$]$_{1-2}$—, —[(CH$_2$)$_{1-2}$C(O)O(CH$_2$)$_{1-2}$]$_{1-2}$—, —[(CH$_2$)$_{1-2}$O(CH$_2$)$_{1-3}$]$_{1-2}$—, —[(CH$_2$)$_{1-2}$C(O)NH(CH$_2$)$_{1-2}$]$_{1-2}$— and —[(CH$_2$)$_{1-2}$NHC(O)(CH$_2$)$_{1-2}$]$_{1-2}$—, wherein one or two hydrogens of each CH$_2$ group may be optionally and independently replaced with a group selected from —CH$_3$ and —OH; each Y$_1$ is —(CH$_2$)$_{1-3}$NH—, —OC(O)(CH$_2$)$_{1-3}$—, —NHC(O)(CH$_2$)$_{1-3}$—, —C(O)O(CH$_2$)$_{1-3}$—, —C(O)NH(CH$_2$)$_{1-3}$—, —(CH$_2$)$_{1-3}$—, or absent; each X is independently —N$^+$(C$_1$-C$_6$alkyl)$_3$, —S(O)$_2$(OH), —OS(O)$_2$(OH), —NHC(=NH)NH$_2$, —OP(O)(OH)$_2$, P(O)(OH)$_2$, —N(C$_1$-C$_6$alkyl)$_2$, or —CO$_2$H; and each RG is isocyanate, thioisocyanate, succinimidyl ester or a succinimidyl carbamate.

In another aspect of the above embodiments, for any one of Formulae (I), (Ia), (Ib), (II), (IIa), (IIb), (III), (IIIa) or (IIIb), each n is an integer from 0 to 4. In one aspect of this embodiment, for any one of Formulae (I), (Ia), (Ib), (II), (IIa), (IIb), (III), (IIIa) or (IIIb), n is 0. In one aspect of this embodiment, for any one of Formulae (I), (Ia), (Ib), (II), (IIa), (IIb), (III), (IIIa) or (IIIb), n is 1. In one aspect of this embodiment, for any one of Formulae (I), (Ia), (Ib), (II), (IIa), (IIb), (III), (IIIa) or (IIIb), n is 2. In one aspect of this embodiment, for any one of Formulae (I), (Ia), (Ib), (II), (IIa), (IIb), (III), (IIIa) or (IIIb), n is 3. In one aspect of this embodiment, for any one of Formulae (I), (Ia), (Ib), (II), (IIa), (IIb), (III), (IIIa) or (IIIb), n is 4.

In yet another aspect of the above embodiments, for any one of Formulae (I), (Ia), (Ib), (II), (IIa), (IIb), (III), (IIIa) or (IIIb), each p is an integer from 0 to 6. In one aspect of this embodiment, for any one of Formulae (I), (Ia), (Ib), (II), (IIa), (IIb), (III), (IIIa) or (IIIb), p is 0. In one aspect of this embodiment, for any one of Formulae (I), (Ia), (Ib), (II), (IIa), (IIb), (III), (IIIa) or (IIIb), p is 1. In one aspect of this embodiment, for any one of Formulae (I), (Ia), (Ib), (II), (IIa), (IIb), (III), (IIIa) or (IIIb), p is 2. In one aspect of this embodiment, for any one of Formulae (I), (Ia), (Ib), (II), (IIa), (IIb), (III), (IIIa) or (IIIb), p is 3. In one aspect of this embodiment, for any one of Formulae (I), (Ia), (Ib), (II), (IIa), (IIb), (III), (IIIa) or (IIIb), p is 4. In one aspect of this embodiment, for any one of Formulae (I), (Ia), (Ib), (II), (IIa), (IIb), (III), (IIIa) or (IIIb), p is 5. In one aspect of this embodiment, for any one of Formulae (I), (Ia), (Ib), (II), (IIa), (IIb), (III), (IIIa) or (IIIb), p is 6.

In still another aspect of the above embodiments, for any one of Formulae (I), (Ia), (Ib), (II), (IIa), (IIb), (III), (IIIa) or (IIIb), each k is an integer from 0 to 6. In another aspect of this embodiment, for any one of Formulae (I), (Ia), (Ib), (II), (IIa), (IIb), (III), (IIIa) or (IIIb), k is 0. In one aspect of this embodiment, for any one of Formulae (I), (Ia), (Ib), (II), (IIa), (IIb), (III), (IIIa) or (IIIb), k is 1. In one aspect of this embodiment, for any one of Formulae (I), (Ia), (Ib), (II), (IIa), (IIb), (III), (IIIa) or (IIIb), k is 2. In one aspect of this embodiment, for any one of Formulae (I), (Ia), (Ib), (II), (IIa), (IIb), (III), (IIIa) or (IIIb), k is 3. In one aspect of this embodiment, for any one of Formulae (I), (Ia), (Ib), (II), (IIa), (IIb), (III), (IIIa) or (IIIb), k is 4. In one aspect of this embodiment, for any one of Formulae (I), (Ia), (Ib), (II), (IIa), (IIb), (III), (IIIa) or (IIIb), k is 5. In one aspect of this embodiment, for any one of Formulae (I), (Ia), (Ib), (II), (IIa), (IIb), (III), (IIIa) or (IIIb), k is 6.

In another aspect of the above embodiments, for any one of Formulae (I), (Ia), (Ib), (II), (IIa), (IIb), (III), (IIIa) or (IIIb), each m is an integer from 0 to 3. In one aspect of this embodiment, for any one of Formulae (I), (Ia), (Ib), (II), (IIa), (IIb), (III), (IIIa) or (IIIb), m is 0. In one aspect of this embodiment, for any one of Formulae (I), (Ia), (Ib), (II), (IIa), (IIb), (III), (IIIa) or (IIIb), m is 1. In one aspect of this embodiment, for any one of Formulae (I), (Ia), (Ib), (II), (IIa), (IIb), (III), (IIIa) or (IIIb), m is 2. In one aspect of this embodiment, for any one of Formulae (I), (Ia), (Ib), (II), (IIa), (IIb), (III), (IIIa) or (IIIb), m is 3.

In yet another aspect of the above embodiments, for any one of Formulae (III), (IIIa) or (IIIb), each R is independently halo, —OH, —CN, C$_1$-C$_3$ alkyl, C$_3$-C$_6$ cycloalkyl, C$_1$-C$_3$ alkoxy, C$_1$-C$_3$ haloalkyl or C$_1$-C$_3$ haloalkoxy. In a further aspect of the above embodiments, for any one of Formulae (III), (IIIa) or (IIIb), R is independently —F or —Cl. In a further aspect of the above embodiments, for any one of Formulae (III), (IIIa) or (IIIb), R is independently methyl. In a further aspect of the above embodiments, for any one of Formulae (III), (IIIa) or (IIIb), R is independently methoxy. In a further aspect of the above embodiments, for any one of Formulae (III), (IIIa) or (IIIb), R is independently —$CF_3$. In a further aspect of the above embodiments, for any one of Formulae (III), (IIIa) or (IIIb), R is independently —$OCF_3$. In a further aspect of the above embodiments, for any one of Formulae (III), (IIIa) or (IIIb), R is independently cyclopropyl.

In still another aspect of the above embodiments, for any one of Formulae (I), (Ia), (Ib), (II), (IIa), (IIb), (III), (IIIa) or (IIIb), $Y_1$ is independently —$(CH_2)_nW(CH_2)_n$—, —OC(O)—$(CH_2)_{1-4}$—, —OC(O)—$(CH_2)_{1-4}$W— or absent. In one aspect of the above embodiments, for any one of Formulae (I), (Ia), (Ib), (II), (IIa), (IIb), (III), (IIIa) or (IIIb), $Y_1$ is absent. In one aspect of the above embodiments, for any one of Formulae (I), (Ia), (Ib), (II), (IIa), (IIb), (III), (IIIa) or (IIIb), $Y_1$ is —OC(O)—$(CH_2)_{1-4}$—. In one aspect of the above embodiments, for any one of Formulae (I), (Ia), (Ib), (II), (IIa), (IIb), (III), (IIIa) or (IIIb), $Y_1$ is —OC(O)—$(CH_2)_{1-4}$W—.

In another aspect of the above embodiments, for any one of Formulae (I), (Ia), (Ib), (II), (IIa), (IIb), (III), (IIIa) or (IIIb), each W is independently $N(C_1-C_6$ alkyl), NH, S or O. In one aspect of the above embodiments, for any one of Formulae (I), (Ia), (Ib), (II), (IIa), (IIb), (III), (IIIa) or (IIIb), each W is independently $N(C_1-C_6$ alkyl). In one aspect of the above embodiments, for any one of Formulae (I), (Ia), (Ib), (II), (IIa), (IIb), (III), (IIIa) or (IIIb), each W is independently NH. In one aspect of the above embodiments, for any one of Formulae (I), (Ia), (Ib), (II), (IIa), (IIb), (III), (IIIa) or (IIIb), each W is independently O. In one aspect of the above embodiments, for any one of Formulae (I), (Ia), (Ib), (II), (IIa), (IIb), (III), (IIIa) or (IIIb), each W is independently S.

In yet another aspect of the above embodiments, for any one of Formulae (I), (Ia), (Ib), (II), (IIa), (IIb), (III), (IIIa) or (IIIb), each Y, Y' and Y" is independently selected from —[$(CH_2)OC(O)(CH_2)_2]_2$—, —[$(CH_2)_2OC(O)(CH_2)]_2$—, —$(CH_2)OC(O)(CH_2)_2$—, —$(CH_2)_2OC(O)(CH_2)$—, —[$(CH_2)C(O)O(CH_2)_2]_2$—, —[$(CH_2)_2C(O)O(CH_2)]_2$—, —$(CH_2)C(O)O(CH_2)_2$—, —$(CH_2)_2C(O)O(CH_2)$—, —[$(CH_2)O(CH_2)_3]_2$—, —$(CH_2)O(CH_2)_3$—, —[$(CH_2)_2O(CH_2)_3]_2$—, —$(CH_2)_2O(CH_2)_3$—, —[$(CH_2)_2O(CH_2)_2]_2$—, —$(CH_2)_2O(CH_2)_2$—, —[$(CH_2)NHC(O)(CH_2)_2]_2$—, —[$(CH_2)_2NHC(O)(CH_2)]_2$—, —$(CH_2)NHC(O)(CH_2)_2$—, —$(CH_2)_2NHC(O)(CH_2)$—, —[$(CH_2)C(O)NH(CH_2)_2]_2$—, —[$(CH_2)_2C(O)NH(CH_2)]_2$—, —$(CH_2)C(O)NH(CH_2)_2$—, and —$(CH_2)_2C(O)NH(CH_2)$—, and wherein one or two hydrogens of each $CH_2$ group may be optionally and independently replaced with a group selected from —$CH_3$ and —OH.

In still another aspect of the above embodiments, for any one of Formulae (I), (Ia), (Ib), (II), (IIa), (IIb), (III), (IIIa) or (IIIb), Y, Y' and Y" are independently absent. In another aspect of the above embodiments, for any one of Formulae (I), (Ia), (Ib), (II), (IIa), (IIb), (III), (IIIa) or (IIIb), Y, Y' and Y" are independently —NH—. In another aspect of the above embodiments, for any one of Formulae (I), (Ia), (Ib), (II), (IIa), (IIb), (III), (IIIa) or (IIIb), Y, Y' and Y" are independently a $C_1-C_6$ alkyl. In another aspect of the above embodiments, for any one of Formulae (I), (Ia), (Ib), (II), (IIa), (IIb), (III), (IIIa) or (IIIb), Y, Y' and Y" are independently —$N(C_1-C_6alkyl)$-. In another aspect of the above embodiments, for any one of Formulae (I), (Ia), (Ib), (II), (IIa), (IIb), (III), (IIIa) or (IIIb), Y, Y' and Y" are independently —[$(CH_2)OC(O)(CH_2)_2]_2$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2OC(O)(CH_2)]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)OC(O)(CH_2)_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2OC(O)(CH_2)$—. In another aspect of the above embodiments, for any one of Formulae (I), (Ia), (Ib), (II), (IIa), (IIb), (III), (IIIa) or (IIIb), Y, Y' and Y" are independently —[$(CH_2)C(O)O(CH_2)_2]_2$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2C(O)O(CH_2)]_2$—. In another aspect of the above embodiments, for any one of Formulae (I), (Ia), (Ib), (II), (IIa), (IIb), (III), (IIIa) or (IIIb), Y, Y' or Y" is —$(CH_2)C(O)O(CH_2)_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2C(O)O(CH_2)$—. In another aspect of the above embodiments, for any one of Formulae (I), (Ia), (Ib), (II), (IIa), (IIb), (III), (IIIa) or (IIIb), Y, Y' and Y" are independently —[$(CH_2)O(CH_2)_3]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)O(CH_2)_3$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2O(CH_2)_3]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2O(CH_2)_3$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2O(CH_2)_2]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2O(CH_2)_2$—. In another aspect of the above embodiments, for any one of Formulae (I), (Ia), (Ib), (II), (IIa), (IIb), (III), (IIIa) or (IIIb), Y, Y' and Y" are independently —[$(CH_2)NHC(O)(CH_2)_2]_2$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2NHC(O)(CH_2)]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)NHC(O)(CH_2)_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2NHC(O)(CH_2)$—. In another aspect of the above embodiments, for any one of Formulae (I), (Ia), (Ib), (II), (IIa), (IIb), (III), (IIIa) or (IIIb), Y, Y' and Y" are independently —[$(CH_2)C(O)NH(CH_2)_2]_2$—. In another aspect of the above embodiments, for any one of Formulae (I), (Ia), (Ib), (II), (IIa), (IIb), (III), (IIIa) or (IIIb), Y, Y' and Y" are independently —[$(CH_2)_2C(O)NH(CH_2)]_2$—. In another aspect of the above embodiments, for any one of Formulae (I), (Ia), (Ib), (II), (IIa), (IIb), (III), (IIIa) or (IIIb), Y, Y' and Y" are independently —$(CH_2)C(O)NH(CH_2)_2$—. In another aspect of the above embodiments, for any one of Formulae (I), (Ia), (Ib), (II), (IIa), (IIb), (III), (IIIa) or (IIIb), Y, Y' and Y" are independently —$(CH_2)_2C(O)NH(CH_2)$—.

In yet another aspect of the above embodiments, for any one of Formulae (I), (Ia), (Ib), (II), (IIa), (IIb), (III), (IIIa) or (IIIb), each instance of X are all the same. In aspect of the above embodiments, for any one of Formulae (I), (Ia), (Ib), (II), (IIa), (IIb), (III), (IIIa) or (IIIb), each X is —$N(C_1-C_6$ alkyl$)_2$. In another aspect of the above embodiments, for any one of Formulae (I), (Ia), (Ib), (II), (IIa), (IIb), (III), (IIIa) or

(IIIb), each X is —N⁺(C₁-C₆ alkyl)₃. In another aspect of the above embodiments, for any one of Formulae (I), (Ia), (Ib), (II), (IIa), (IIb), (III), (IIIa) or (IIIb), each X is —N(CH₃)₂. In another aspect of the above embodiments, for any one of Formulae (I), (Ia), (Ib), (II), (IIa), (IIb), (III), (IIIa) or (IIIb), each X is —N(CH₂CH₃)₂. In another aspect of the above embodiments, for any one of Formulae (I), (Ia), (Ib), (II), (IIa), (IIb), (III), (IIIa) or (IIIb), each X is —CO₂H. In another aspect of the above embodiments, for any one of Formulae (I), (Ia), (Ib), (II), (IIa), (IIb), (III), (IIIa) or (IIIb), each X is —CO₂CH₃ or —CO₂(CH₂CH₃). In another aspect of the above embodiments, for any one of Formulae (I), (Ia), (Ib), (II), (IIa), (IIb), (III), (IIIa) or (IIIb), each X is —S(O)(OH)₂. In another aspect of the above embodiments, for any one of Formulae (I), (Ia), (Ib), (II), (IIa), (IIb), (III), (IIIa) or (IIIb), each X is —OS(O)(OH)₂. In another aspect of the above embodiments, for any one of Formulae (I), (Ia), (Ib), (II), (IIa), (IIb), (III), (IIIa) or (IIIb), each X is —NHC(=NH)NH₂. In another aspect of the above embodiments, for any one of Formulae (I), (Ia), (Ib), (II), (IIa), (IIb), (III), (IIIa) or (IIIb), each X is —OP(O)(OH)₂. In another aspect of the above embodiments, for any one of Formulae (I), (Ia), (Ib), (II), (IIa), (IIb), (III), (IIIa) or (IIIb), each X is —P(O)(OH)₂. In another aspect of the above embodiments, for any one of Formulae (I), (Ia), (Ib), (II), (IIa), (IIb), (III), (IIIa) or (IIIb), each X is —C(O)N(C₁-C₆alkyl)₂. In another aspect of the above embodiments, for any one of Formulae (I), (Ia), (Ib), (II), (IIa), (IIb), (III), (IIIa) or (IIIb), each X is —C(O)NH₂. In another aspect of the above embodiments, for any one of Formulae (I), (Ia), (Ib), (II), (IIa), (IIb), (III), (IIIa) or (IIIb), each X is —C(O)NH(C₁-C₆alkyl). In another aspect of the above embodiments, for any one of Formulae (I), (Ia), (Ib), (II), (IIa), (IIb), (III), (IIIa) or (IIIb), each X is —NHC(O)(C₁-C₆alkyl). In another aspect of the above embodiments, for any one of Formulae (I), (Ia), (Ib), (II), (IIa), (IIb), (III), (IIIa) or (IIIb), each X is —C(O)(OC₁-C₆alkyl).

In another embodiment, for any one of Formulae (I), (Ia), (Ib), (II), (IIa), (IIb), (III), (IIIa) or (IIIb), RG is a succinimidyl ester group. In one embodiment, for any one of Formulae (I), (Ia), (Ib), (II), (IIa), (IIb), (III), (IIIa) or (IIIb), RG is a succinimidyl carbamate group. In another embodiment, for any one of Formulae (I), (Ia), (Ib), (II), (IIa), (IIb), (III), (IIIa) or (IIIb), RG is an isocyanate group. In another embodiment, for any one of Formulae (I), (Ia), (Ib), (II), (IIa), (IIb), (III), (IIIa) or (IIIb), RG is a thioisocyanate group. In another embodiment, for any one of Formulae (I), (Ia), (Ib), (II), (IIa), (IIb), (III), (IIIa) or (IIIb), RG is a carboxylic acid group. In another embodiment, for any one of Formulae (I), (Ia), (Ib), (II), (IIa), (IIb), (III), (IIIa) or (IIIb), RG is an amine group. In another embodiment, for any one of Formulae (I), (Ia), (Ib), (II), (IIa), (IIb), (III), (IIIa) or (IIIb), RG is an aldehyde group.

In yet another embodiment, the present disclosure relates to use of a chemical tag according to one of Formulae (IV), (V), (VI), (VII), (VIII) or (IX):

(IV)

(V)

(VI)

(VII)

-continued (VIII)

(IX)

or a salt thereof; wherein each Q is N($C_1$-$C_3$alkyl), NH or O; each T is H, methyl or —OH; each $Y_1$ is —($CH_2$)$_{1-3}$NH—, —OC(O)($CH_2$)$_{1-3}$—, —NHC(O)($CH_2$)$_{1-3}$—, —C(O)O($CH_2$)$_{1-3}$—, —C(O)NH($CH_2$)$_{1-3}$—, —($CH_2$)$_{1-3}$—, or absent; each X is independently —$N^+$($C_1$-$C_6$alkyl)$_3$, —S(O)(OH)$_2$, —OS(O)(OH)$_2$, —NHC(=NH)$NH_2$, —OP(O)(OH)$_2$, —P(O)(OH)$_2$, —N($C_1$-$C_6$alkyl)$_2$, or —$CO_2$H; and each RG is isocyanate, thioisocyanate, succinimidyl ester or a succinimidyl carbamate.

In one aspect of the above embodiments, for any one of Formulae (I), (Ia), (Ib), (III), (IIIa), (IIIb), (VII) or (VIII) Z is N. In another aspect of the above embodiments, for any one of Formulae (I), (Ia), (Ib), (III), (IIIa), (IIIb), (VII) or (VIII), Z is CH.

In another aspect of the above embodiments, for Formula (VI), each T is —H. In one aspect of the above embodiments, for Formula (VI), each T is —OH. In one aspect of the above embodiments, for Formula (VI), each T is —$CH_3$.

In yet another aspect of the above embodiments, for any one of Formulae (IV), (V), (VI), (VII), (VIII), or (IX), each instance of X are all the same. In aspect of the above embodiments, for any one of Formulae (IV), (V), (VI), (VII), (VIII), or (IX), each X is —N($C_1$-$C_6$ alkyl)$_2$. In another aspect of the above embodiments, for any one of Formulae (IV), (V), (VI), (VII), (VIII), or (IX), each X is —$N^+$($C_1$-$C_6$ alkyl)$_3$. In another aspect of the above embodiments, for any one of Formulae (IV), (V), (VI), (VII), (VIII), or (IX), each X is —N($CH_3$)$_2$. In another aspect of the above embodiments, for any one of Formulae (IV), (V), (VI), (VII), (VIII), or (IX), each X is —N($CH_2CH_3$)$_2$. In another aspect of the above embodiments, for any one of Formulae (IV), (V), (VI), (VII), (VIII), or (IX), each X is —$CO_2$H. In another aspect of the above embodiments, for any one of Formulae (IV), (V), (VI), (VII), (VIII), or (IX), each X is —S(O)(OH)$_2$. In another aspect of the above embodiments, for any one of Formulae (IV), (V), (VI), (VII), (VIII), or (IX), each X is —OS(O)(OH)$_2$. In another aspect of the above embodiments, for any one of Formulae (IV), (V), (VI), (VII), (VIII), or (IX), each X is —NHC(=NH)$NH_2$. In another aspect of the above embodiments, for any one of Formulae (IV), (V), (VI), (VII), (VIII), or (IX), each X is —OP(O)(OH)$_2$. In another aspect of the above embodiments, for any one of Formulae (IV), (V), (VI), (VII), (VIII), or (IX), each X is —P(O)(OH)$_2$.

In still another embodiment, for any one of Formulae (IV), (V), (VI), (VII), (VIII), or (IX), RG is a succinimidyl ester group. In one embodiment, for any one of Formulae (IV), (V), (VI), (VII), (VIII), or (IX), RG is a succinimidyl carbamate group. In another embodiment, for any one of Formulae (IV), (V), (VI), (VII), (VIII), or (IX)), RG is an isocyanate group. In another embodiment, for any one of Formulae (IV), (V), (VI), (VII), (VIII), or (IX), RG is a thioisocyanate group.

In another aspect of the above embodiments, for any one of Formulae (IV), (V), (VI), (VII), (VIII), or (IX), each $Y_1$ is independently —($CH_2$)$_{1-3}$NH—, —OC(O)($CH_2$)$_{1-3}$—, —NHC(O)($CH_2$)$_{1-3}$—, —C(O)O($CH_2$)$_{1-3}$—, —C(O)NH($CH_2$)$_{1-3}$—, —($CH_2$)$_{1-3}$—, or absent. In one aspect of the above embodiments, for any one of Formulae (IV), (V), (VI), (VII), (VIII), or (IX), $Y_1$ is absent. In one aspect of the above embodiments, for any one of Formulae (IV), (V), (VI), (VII), (VIII), or (IX), $Y_1$ is —$CH_2$—. In one aspect of the above embodiments, for any one of Formulae (IV), (V), (VI), (VII), (VIII), or (IX), $Y_1$ is —$CH_2CH_2$—. In one aspect of the above embodiments, for any one of Formulae (IV), (V), (VI), (VII), (VIII), or (IX), $Y_1$ is —($CH_2$)$_3$—. In one aspect of the above embodiments, for any one of Formulae (IV), (V), (VI), (VII), (VIII), or (IX), $Y_1$ is —$CH_2$NH—. In one aspect of the above embodiments, for any one of Formulae (IV), (V), (VI), (VII), (VIII), or (IX), $Y_1$ is —$CH_2CH_2$NH—. In one aspect of the above embodiments, for any one of Formulae (IV), (V), (VI), (VII), (VIII), or (IX), $Y_1$ is —($CH_2$)$_3$NH—. In one aspect of the above embodiments, for any one of Formulae (IV), (V), (VI), (VII), (VIII), or (IX), $Y_1$ is —OC(O)$CH_2$—. In one aspect of the above embodiments, for any one of Formulae (IV), (V), (VI), (VII), (VIII), or (IX), $Y_1$ is —OC(O)$CH_2CH_2$—. In one aspect of the above embodiments, for any one of Formulae (IV), (V), (VI), (VII), (VIII), or (IX), $Y_1$ is —OC(O)($CH_2$)$_3$—. In one aspect of the above embodiments, for any one of Formulae (IV), (V), (VI), (VII), (VIII), or (IX), $Y_1$ is —NHC(O)$CH_2$—. In one aspect of the above embodiments, for any one of Formulae (IV), (V), (VI), (VII), (VIII), or (IX), $Y_1$ is —NHC(O)$CH_2CH_2$—. In one aspect of the above embodiments, for any one of Formulae (IV), (V), (VI), (VII), (VIII), or (IX), $Y_1$ is —NHC(O)($CH_2$)$_3$—. In one aspect of the above embodiments, for any one of Formulae (IV), (V), (VI), (VII), (VIII), or (IX), $Y_1$ is —C(O)O$CH_2$—. In one aspect of the above embodiments, for any one of Formulae (IV), (V), (VI), (VII), (VIII), or (IX), $Y_1$ is —C(O)O$CH_2CH_2$—. In one aspect of the above embodiments, for any one of Formulae (IV), (V), (VI), (VII), (VIII), or (IX), $Y_1$ is —C(O)O($CH_2$)$_3$—. In one aspect of the above embodiments, for any one of Formulae (IV), (V), (VI), (VII), (VIII), or (IX), $Y_1$ is —C(O)NH$CH_2$—. In one aspect of the above embodiments, for any one of Formulae (IV), (V), (VI), (VII), (VIII), or (IX), $Y_1$ is —C(O)NH$CH_2CH_2$—. In one aspect of the above embodiments, for any one of Formulae (IV), (V), (VI), (VII), (VIII), or (IX), $Y_1$ is —C(O)NH($CH_2$)$_3$—.

The present disclosure includes use of compounds according to any of Formulae (I), (Ia), (Ib), (II), (IIa), (IIb), (III), (IIIa), (IIIb), (IV), (V), (VI), (VII), (VIII) and (IX) as chemical tags in the disclosed methods, wherein the particular value for any of the variables Y, Y', Y'', Y1, X, W, RG, Z, R, n, p, k, m, Q, and T, where present, may be combined with any other particular value for the remaining variables, as disclosed above.

The present disclosure also includes compounds according to any of Formulae (I), (Ia), (Ib), (II), (IIa), (IIb), (III), (IIIa), (IIIb), (IV), (V), (VI), (VII), (VIII) and (IX).

In one embodiment, wherein the chemical tag is a dendrimer type molecule, the dendrimer is a polyamindoamine (PAMAM), polypropyleneimine (PPI) a polyglutamic acid and/or a polyester dendrimer.

In another embodiment of the present invention, the chemical tag is selected from the group consisting of:

or a salt thereof.

In a further embodiment, the chemical tag is selected from:

or a salt thereof; wherein each $R^3$ is independently $C_1$-$C_6$ alkyl; and each $R^4$ is independently —H or $C_1$-$C_6$ alkyl. In one aspect of this embodiment, each $R^3$ is methyl and each $R^4$ is H or methyl. In another aspect of this embodiment, each $R^3$ is methyl and each $R^4$ is H.

Dendrimer-type compounds of formulae (I), (Ia), (Ib), (II), (IIa), (IIb), (III), (IIIa), (IIIb), (IV), (V), (VI), (VII), (VIII), and (IX) can be made according the methods known in the art. See, e.g., Tomalia et al., *A New Class of Polymers: Starburst-Dendritic Macromolecules*, Polymer Journal (1985), 17:117-132; Tomalia et al., *Poly(amidoamine) (PAMAM) Dendrimers: from biomimicry to drug delivery and biomedical applications*, Drug Discovery Today (2001), 15:427-436; Newkome et al., *Micelles, Part I. Cascade Molecules: a new approach to micelles*, J. Org. Chem. (1985), 50(11):2003-2004; and Hawker et al., *Preparation of Polymers with Controlled Molecular Architecture*, J. Am. Chem. Soc. (1990), 112(21):7638-7647; Klajnert, Barbara and Bryszewska, Maria; *Dendrimers: Properties and Applications*, Acta Biochimica Polonica, (2001) 48(1):199-208.

Additional compounds of formulae (I), (Ia), (Ib), (II), (IIa), (IIb), (III), (IIIa), (IIIb), (IV), (V), (VI), (VII), (VIII), and (IX) can be synthesized using standard organic methodologies, with use of standard protection/deprotection techniques as necessary. See Nicolaou, K. C.; Sorensen, E. J. (1996), *Classics in Total Synthesis*. New York: VCH; March, J.; Smith, D, (2001), *Advanced Organic Chemistry*, 5th ed. New York: Wiley; Clayden, Jonathan; Greeves, Nick; Warren, Stuart; Wothers, Peter, (2000), *Organic Chemistry*, Oxford University Press.

Separation of Lipid Ions

Ion Mobility (IM) & Capillary Electrophoresis (CE)

IM is a gas-phase electrophoretic technique that enables the separation of gas-phase lipid ions within a chamber pressurized with a buffer gas (e.g., nitrogen). Capillary electrophoresis is an electrokinetic separation method performed in sub-millimeter capillaries and in micro- and nanofluidic channels.

In one embodiment, the present disclosure includes separation of components of a sample based on charge state using either ion mobility (IM).

During IM, the time required for lipid ions to cross the ion-mobility separation cell—the drift time—depends principally on the collision frequency between the ions and the buffer gas. Thus drift times are directly related to the shape, size, and charge of the component ions as well as to the nature of the buffer gas. From the characteristic time that a component ion takes to cross the ion mobility separation cell (drift time), it is possible to calculate the rotationally-averaged collision cross section (CCS), which represents the effective area for the interaction between an individual ion and the neutral gas through which it travels. CCS, an important physicochemical property of compounds, is related to chemical structure and three-dimensional conformation. Changing the size of the chemical tag will alter the CCS value for any tagged component in a sample. Thus, the present disclosure allows for selective increase of the CCS value for components in a sample by using bulkier chemical tags. By controlling the charge and the size of the chemical tag, it may be possible to significantly affect the separation of the components of a sample in order to better quantify and characterize them. In other words, IM allows separating multiply charged molecules by their charge status, pulling them apart from the rest of the molecules in the sample, and use of further analysis using CCS data can improve their identification, quantification and/or spatial localization. See FIG. 1 which shows doubly and triply charged lipid ions being specifically delineated from a sample containing a multitude of singly charged ion species.

Components in a sample may localize in different compositions and concentrations across its surface. Imaging of samples (analyzing using the techniques disclosed herein) may allow topographic mapping (i.e., spatial localization) of distinct components in a sample (e.g., cell cultures and tissue sections). For example, in a typical IM-MS imaging experiment, a focused excitatory beam (e.g., laser or a stream of charged solvent droplets) is directed at the biological sample to scan the surface along a user defined two dimensional array. Upon impact of the excitatory beam, biomolecular ions are desorbed and ionized from the sample surface and directed into the mass spectrometer. The addition of IM to a typical MS imaging experiment allows separation of the components of interest from the interfering background before MS detection, resulting in a greater signal-to-noise ratio and more accurate localization of the same. In one embodiment, IM is followed by identification of the components of the sample using UV spectroscopy, flame ion detection, Raman spectroscopy, or nuclear quadrupole resonance.

In another embodiment, the present disclosure includes analyzing a sample, comprising selectively reacting one or more component in the sample with a chemical tag which has two or more sites for ionization, separating components using ion mobility spectrometry or capillary electrophoresis, and analyzing the sample at a plurality of different locations and identifying the components contained in location sampled. In one aspect of this embodiment, the components are first separated using IM, and then analyzed using MS. In another aspect of this embodiment, the data collected by the method for each location is used to determine the spatial localization of molecules in the sample. In one aspect of these embodiments, the biological sample is a tissue section or a cell culture.

Capillary electrophoresis (CE) may refer to capillary zone electrophoresis (CZE), capillary gel electrophoresis (CGE), capillary isoelectric focusing (LIEF) and/or capillary isotachophoresis and micellar electrokinetic chromatography (MEKC). Separation of ionized species occurs due to their electrophoretic mobility. In one embodiment, the present disclosure relates to use of capillary electrophoresis for separation of components of a sample based on charge status. In one aspect of this embodiment, the CE is CZE. In another aspect of this embodiment, the CE is CGE. In a further aspect of this embodiment, the CE is CLEF. In a final aspect of this embodiment, the CE is MEKC. In any of these embodiments, the CE may be performed on a capillary array electrophoresis instrument.

In one embodiment, when separation of the ionized components is done using IM, the present disclosure relates to use of drift time ion mobility spectrometry (DT-IMS), traveling wave ion mobility spectrometry (TW-IMS), or differential mobility spectrometry (DMS), which is also known as field-asymmetric ion-mobility spectrometry (FAIMS), for the separation of ionized molecules of a sample according to the ion mobility of the ionized molecules. In one aspect of this embodiment, the ionized molecules are separated according to ion mobility based on the charge state of the ionized molecules.

In one embodiment, the present method includes the additional step of ionizing the components in the biological sample to be analyzed prior to the separation of the ionized molecules of the sample according to their charge state. In one aspect of this embodiment, the ionization step must result in ionization of at least two or more potential sites of ionization on the chemically tagged components in a sample. In one aspect of this embodiment, the ionization may be achieved using electrospray ionization (ESI) or desorption electrospray ionization (DESI). In one aspect of this embodiment, the ionization step includes electrospray ionization. In one embodiment, the ionization step occurs after the selective reaction of a component in a sample with a chemical tag which has two or more sites for ionization.

Identification of Sample Components

In one embodiment, the present method includes identification of the components of the sample using an analytical technique such as UV spectroscopy, flame ion detection, Raman spectroscopy, nuclear quadropole resonance (NQR), or mass spectrometry (MS). In another embodiment, the sample is analyzed to determine the identities of the components therein using MS.

In one embodiment, the present method includes the separation of the components in the sample is done using ion-mobility spectrometry (IM) and the analysis of the components of the sample is done using MS.

Mass Spectrometry (MS)

Mass spectrometry (MS) is an analytical technique that measures the mass-to-charge ratio of a charged molecule or molecule fragments formed from a sample. MS is used to analyze the mass, chemical composition, and/or chemical structure of a component in a sample of interest. In general, MS includes three steps: ionizing a sample to form charged molecules or molecule fragments (i.e., ions); separating the ions based on their mass-to-charge ratio; and detecting the separated ions to form a mass-to-charge signal (i.e., spectra).

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and Matrix Assisted Laser Desorption Ionization (MALDI). ESI and MALDI are the two most commonly employed methods to ionize proteins for mass spectrometric analysis. ESI and APC1 are the most commonly used ion source techniques for LC/MS (Lee, M. "LC/MS Applications in Drug Development" (2002) J. Wiley & Sons, New York).

Various desorption ionization techniques have been combined IM and MS for imaging of complex molecules, such as lipids, including matrix-assisted laser desorption ionization (MALDI), desorption electrospray ionization (DESI), rapid evaporative ionization MS, and laser ablation electrospray ionization (LAESI). Any one of these technique may be used in the present method, when analysis and identification of the components of the sample is done using mass spectrometry (MS). Any one of these techniques may be used in the present method, when analysis and identification of the components of the sample is done using mass spectrometry (MS). In one embodiment, the present disclosure includes the additional step of ionizing the molecules in the biological sample to be analyzed prior to the separation of the ionized molecules of the sample according to their charge state, wherein the ionization step is done using desorption electrospray ionization or laser ablation electrospray ionization. In one embodiment, the method is performed using LAESI.

In one embodiment, the method is performed using LAESI. In another embodiment, the method is performed using DESI. In yet another embodiment, the method is performed using rapid evaporative ionization MS. In still another embodiment, the method is not performed using MALDI.

Commercially available mass spectrometers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

In another embodiment, the present disclosure includes the additional step of ionizing the molecules in the biological sample to be analyzed prior to the separation of the ionized molecules of the sample according to their charge state, wherein the ionization step is done using desorption electrospray ionization or laser ablation electrospray ionization.

Collision Cross Section (CCS)

Collision cross section (CCS) values are derived from ion mobility measurements. All of the first order equations governing ion mobility apply at low electric fields. Uniform field drift tube designs typically operate at low electric field resulting in very predictable and accurate mobility measurements. Conventional uniform field drift tube ion mobility provides a direct method to calculate collision cross sections (W) using the Mason-Schamp equation given below:

$$\Omega = \frac{(18\pi)^{1/2}}{16} \frac{ze}{(k_b T)^{1/2}} \left[ \frac{1}{m_I} + \frac{1}{m_B} \right]^{1/2} \frac{t_d E}{L} \frac{760}{P} \frac{T}{273.2} \frac{1}{N}$$

where $\Omega$ is the rotationally averaged collision cross section, $k_b$ is the Boltzman constant, T is the temperature of the buffer gas, $m_I$ is the mass of analyte ion, $m_B$ is the mass of buffer gas molecules, $t_d$ is the corrected drift time, ze is the charge state of the analyte ion, E is the electric field, L is the length of the drift cell, P is the pressure in drift cell, and N is the number density in the drift cell. It is important to note that $t_d$ can be determined from the total ion drift time. Once $t_d$ values are calculated they can be used to directly generate CCS measurements.

The accuracy to which the collision cross section can be calculated is determined by the extent to which experimental parameters (pressure, temperature and electric field) are maintained during the mobility experiment. Any time the ion spends outside of the defined drift region produces "end effects," which cause loss of measurement accuracy. Measurements of CCS within 2% accuracy or less can be routinely achieved using uniform field drift tubes. In one embodiment, the present disclosure relates to calculating a collisional cross section (CCS) value for the ionized components, wherein the CCS value assigned for each molecule assists in the identification of the components of the sample. In addition to accurate mass, the experimental CCS of each detected component ion can be searched against CCS databases, to support identification. In one embodiment, components with chemical tags may have their CCS values selectively increased by reacting them with chemical tags of selected weight. In one aspect of this embodiment, CCS values are selectively increased by reacting components with chemical tags of increasing size and weight. Identification and characterization of the components of the sample may thus be enhanced using the present method.

UV Spectroscopy

UV spectroscopy refers to absorption spectroscopy or reflectance spectroscopy in the ultraviolet-visible region. It employs light in the visible, near-UV and near-infrared ranges to excite the components being exposed to the light. The absorption or reflectance in the visible range directly affects the perceived color of the chemicals involved. This technique is analogous to fluorescence spectroscopy, except that fluorescence deals with transitions from the excited state to the ground state, and absorption measures transitions from the ground state to the excited state. In one embodiment of the present method, the sample is analyzed using UV spectroscopy after the separation by ion mobility spectroscopy or capillary electrophoresis to identify and possibly quantify the individual components of the sample.

Flame Ionization Detection (FID)

A flame ionization detector is an analytical instrument that measures the concentration of organic species in a gas stream. It is frequently used as a detector in gas chromatography. In one embodiment of the present method, the sample is analyzed using flame ion detection after the separation by ion mobility spectroscopy or capillary electrophoresis to identify and possibly quantify the individual components of the sample.

Raman Spectroscopy

Raman spectroscopy is a spectroscopic technique used to identify molecules by their characteristic vibrational, rotational and other low-frequency modes. Raman spectroscopy as applies to the present method, includes surface-enhanced Raman, resonance Raman, tip-enhanced Raman, polarized Raman, stimulated Raman, transmission Raman, spatially offset Raman, and hyper Raman. In one embodiment of the present method, the sample is analyzed using Raman spectroscopy after the separation by ion mobility spectroscopy or capillary electrophoresis to identify and possibly quantify the individual components of the sample.

Nuclear Quadropole Resonance (NQR)

Nuclear quadropole resonance (NQR) is an analytic technique similar to NMR, except that the nuclei are excited by the interaction of an electric field gradient and the quadropole moment of the nuclear charge distribution. Each molecule has a unique NQR signal, and thus the method can be employed to specifically identify components of a sample. In one embodiment of the present method, the sample is analyzed using nuclear quadropole resonance after the separation by ion mobility spectroscopy or capillary electrophoresis to identify and possibly quantify the individual components of the sample.

Biological Samples

Biological samples can include any sample that is derived from the body of a subject. In this context, the subject can be an animal, for example a mammal, for example a human. Other exemplary subjects include a mouse, rat, guinea-pig, rabbit, cat, dog, goat, sheep, pig, cow, or horse. The individual can be a patient, for example, an individual suffering from a disease or being suspected of suffering from a disease. A biological sample can be a bodily fluid or tissue, for example taken for the purpose of a scientific or medical test, such as for studying or diagnosing a disease (e.g., by detecting and/or identifying a pathogen or the presence of a biomarker). Biological samples can also include cells, for example, pathogens or cells of the individual biological sample (e.g., tumor cells). Such biological samples can be obtained by known methods including tissue biopsy (e.g., punch biopsy) and by taking blood, bronchial aspirate, sputum, urine, feces, or other body fluids. Exemplary biological samples include humor, whole blood, plasma, serum, umbilical cord blood (in particular, blood obtained by percutaneous umbilical cord blood sampling (PUBS)), cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract.

In one embodiment, the sample is a blood sample, such as a dried blood spot. In another embodiment, the sample is a blood-derived sample, such as plasma or serum.

In another embodiment, the sample is a cell sample. The cell sample can contain material obtained or derived from a subject. In other embodiments, the cell sample can contain cells from an in vitro or ex vivo cell culture. In other embodiments, the sample is a cell supernatant sample.

EXAMPLES

Example 1

Figure 1:
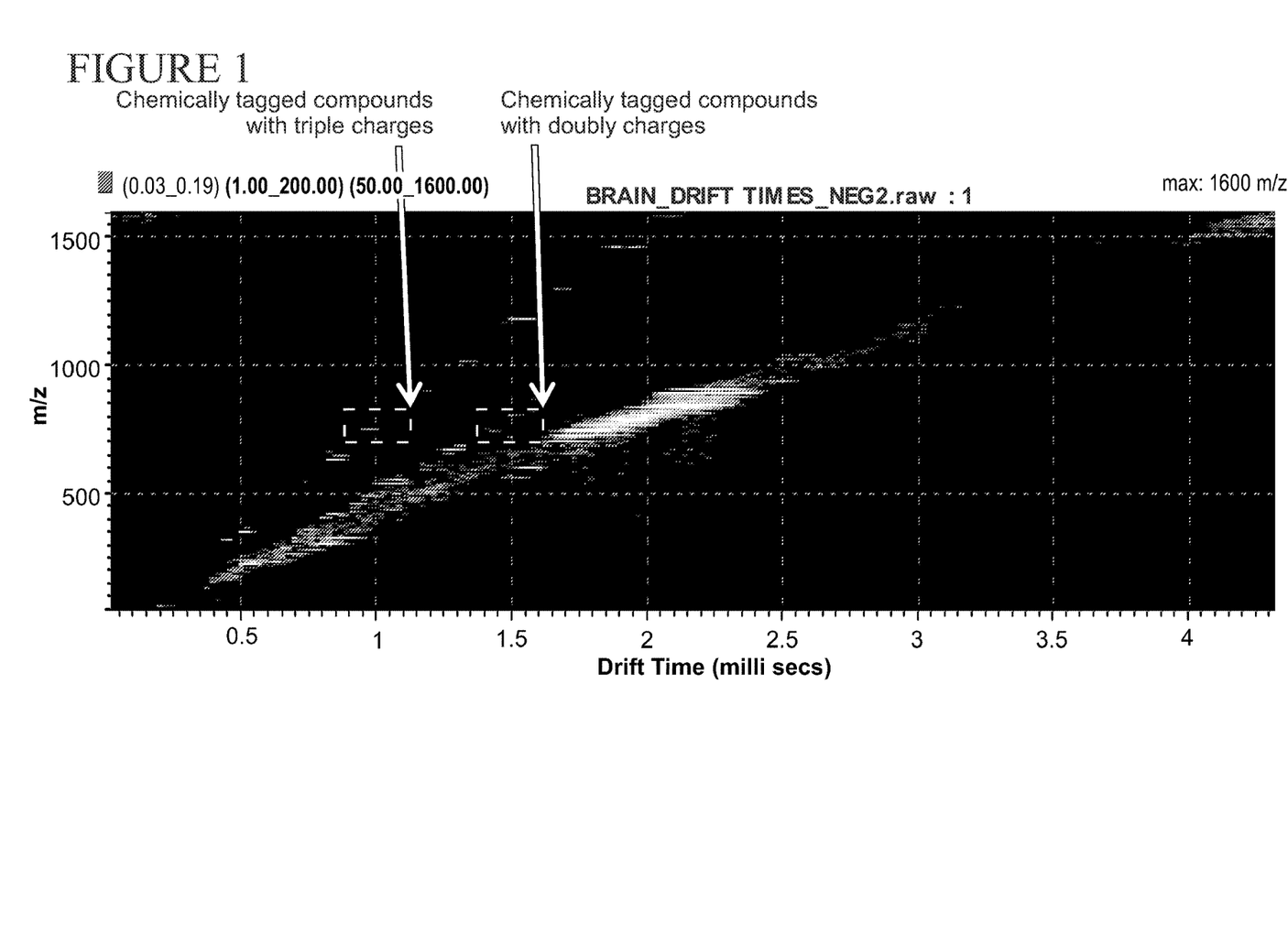
FIG. 1 shows analysis of brain extract using an IM-MS instrument; triply charged and doubly charged ions are highlighted on the figure.

Ionization sources based on electrospray (ESI), including DESI and LAESI, yields multiply charged ions. Charge separation provides that the components in the sample are isolated separate from all other similar species based on charge state. FIG. 1 shows how charge state can be effectively utilized to separate specific lipids out of a complex sample based on charge state alone.

To exploit the use of CCS information of multiple charged ions to improve MS-imaging applications, we analyzed human brain samples using LAESI coupled to a IM-MS instrument. (See FIG. 1). Using CCS information allowed for the isolation of lipids from metabolites, multiply charged proteins and peptides, and from the background ions associated with atmospheric ionization. Identities of 93 lipid species were confirmed using a combination of mass and CCS measurements. (FIG. 1, top).

Topographical maps representing the lipid ion distribution in sub-regions of the human brain were created for selected mass and CCS values present in grey matter and white matter. The use of ion mobility allowed the spatial separation of isobaric lipid species with different CCS values, improving the quality of the signal-to-noise ratio. Notably, only by using this approach was it possible to determine the selective spatial localization of gangliosides in the grey matter versus white matter. These results indicate that CCS information of multiple charged ions may be a significant tool supporting lipid identification and localization in MS imaging studies. See FIG. 1 bottom, which clearly show that use of the IM-MS methodology of the present disclosure leads to greatly enhanced accuracy and precision for measuring the spatial localization of components in tissue cross sections.

Example 2

Figure 2:
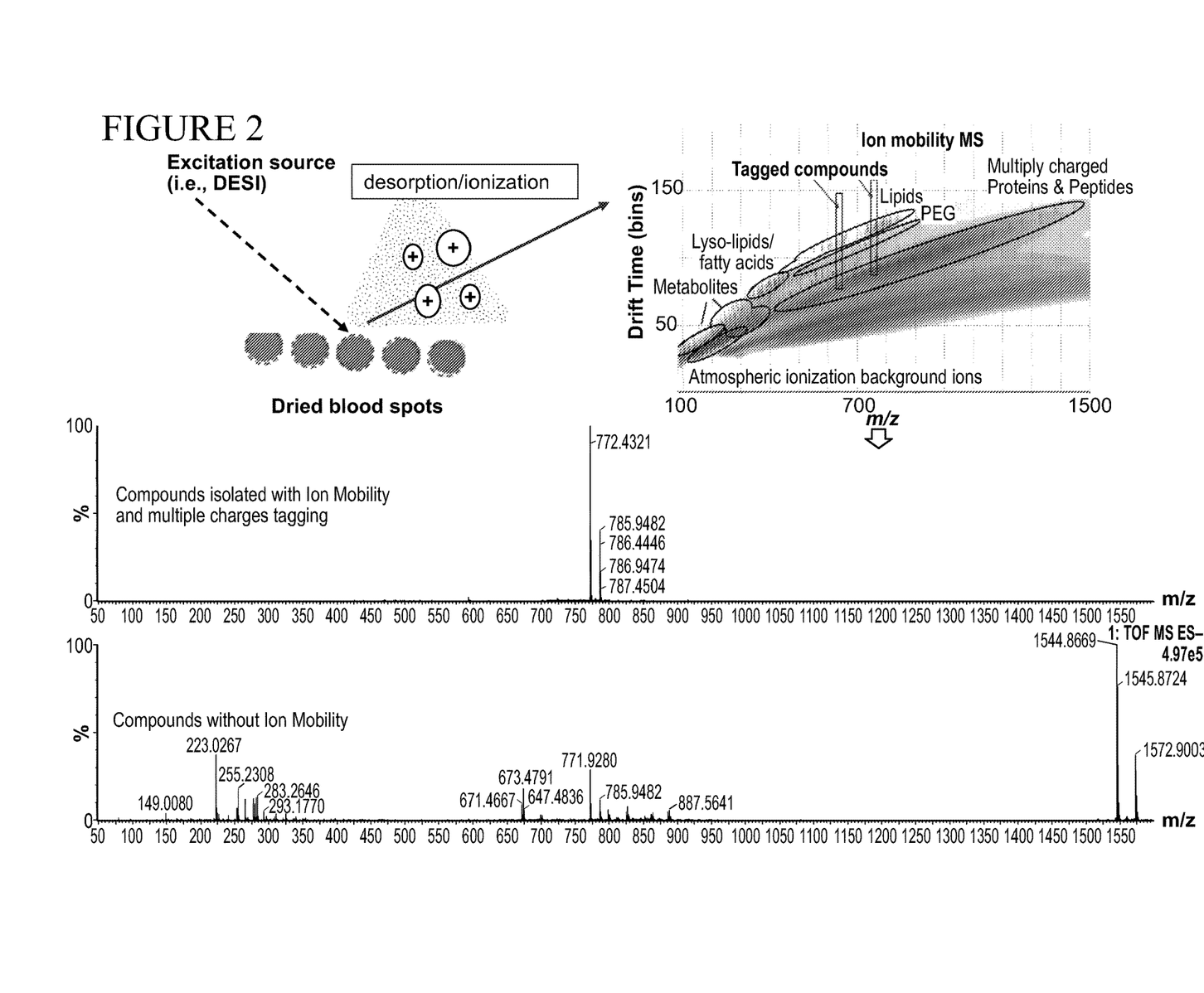
FIG. 2 shows real time analysis of dried blood spots using DESI ionization, separation by ion mobility and MS characterization.

FIG. 2 shows a direct analysis of gangliosides from dried blood spots (DBS) by DESI. Imaging was done using a SYNAPT G2-Si HDMS (WATERS®) equipped with a 2D-DESI source. FIG. 2 also shows that multiply charged ions are clearly separated from the sample using the combined technique IM-MS, whereas characterization of individual components was not at all effective without ion mobility separation.

Data was generated and analyzed using WATERS® High Definition Imaging Software (HDI) 1.35. Spray conditions were as follows: flow rate of 1 μL/min, with a 98% methanol in water mixture at 100 psi $N_2$ gas pressure and a voltage of 5 kV for both polarities. The scan time was 1 second. Gangliosides and cardiolipins (not shown) were separated out as doubly charged ion species, which allowed them to be isolated using ion mobility against interfering ions.

We claim:

1. A compound selected from:

or a salt thereof; wherein
each $R^3$ is independently $C_1$-$C_6$ alkyl; and
each $R^4$ is independently —H or $C_1$-$C_6$ alkyl.

2. The compound of claim 1, or a salt thereof, wherein each $R^3$ is methyl and each $R_4$ is H or methyl.

3. A compound for use as a chemical tag according to claim 1 or claim 2.

* * * * *